US005925334A

United States Patent [19]

Rubin et al.

[11] Patent Number: 5,925,334

[45] Date of Patent: Jul. 20, 1999

[54] USE OF SURFACE ACTIVE AGENTS TO PROMOTE MUCUS CLEARANCE

[76] Inventors: Bruce K. Rubin, 2140 Royall Dr., Winston-Salem, N.C. 27106; Michael T Newhouse, 436 Queen St., Hamilton, Canada, L8P 3T9

[21] Appl. No.: 08/918,112

[22] Filed: Aug. 27, 1997

[51] Int. Cl.[6] .................................................. A61K 9/12

[52] U.S. Cl. ............................. 424/45; 424/46; 514/826; 514/851

[58] Field of Search ........................ 424/45, 46; 514/851, 514/826

[56] References Cited

FOREIGN PATENT DOCUMENTS 0518600 12/1992 European Pat. Off. .

OTHER PUBLICATIONS

Moré et al. (1993). Aerosols in Medicine: Principles, Diagnosis and Therapy. Elsevier Science Publishers, pp. 303–319.

*Primary Examiner*—Raj Bawa

*Attorney, Agent, or Firm*—Robert M. Wolters

[57] ABSTRACT

This disclosure is of a surfactant mixed with an aerosollizing agent, and deposited by such agent, as a treatment for airway obstruction. It has been extensively tested, and has proved successful. It has been hypothesized that the addition of a hypersmolor drug will help to minimize mucus in the airways.

3 Claims, No Drawings

USE OF SURFACE ACTIVE AGENTS TO PROMOTE MUCUS CLEARANCE

BACKGROUND OF INVENTION

Surfactants are surface-active agents. This is customarily used to indicate that these are agents that reduce surface tension at an interface between two different materials. In industry, surfactants have long been used as emulsifiers, detergents, lubricants, and wetting agents. Specialized surface-active agents have been developed for these and many other commercial uses.

For more than 40 years we have also known that the body produces surfactants and that these are critical to the optimal performance particularly of the respiratory system. Close to the time of birth, the developing lung is producing more and more pulmonary surfactant in the distal airways (alveoli) and this surfactant prevents these tiny airways from collapsing with each breath. Babies born prematurely often have insufficient production of pulmonary surfactant to keep the lungs open with each breath and this condition is called respiratory distress syndrome of the newborn. Because this disease claims the lives of thousands of prematurely born babies in the United States every year, many investigators have actively identified the components of pulmonary surfactant and developed a variety of surfactant products for administration to the prematurely born infant. This strategy has proven to be highly successful and has drastically reduced mortality in these tiniest of babies. Commercial products developed as pulmonary surfactant for newborns all include the phospholipid chemical, dipalmitoyl phosphatidylcholine (DPPC) as well as spreading agents that either occur naturally (surfactant associated proteins) or that are made artificially. Commercially available pulmonary surfactants are either made by extraction of natural surfactant from newborn animal lungs, generally cows or pigs (Survanta, Curosurf, Infasurf, BLIS), or made entirely in the laboratory from DPPC with other drugs added to enhance spreading, (Exosurf, KL4). All of these agents have been demonstrated to be effective and sale in the treatment of respiratory distress syndrome of the newborn. Pulmonary surfactants have also been administered to a large number of adults with severe respiratory failure due to a condition known as adult respiratory distress syndrome (ARDS). Despite laboratory confirmation that pulmonary surfactant is inactivated in this condition, these clinical trials have generally proven to be disappointing.

The (B. K.) research laboratory* has long focused on understanding the mechanisms of mucus secretion and clearance. In persons with a chronic inflammatory lung diseases including cystic fibrosis, chronic bronchitis, diffuse panbronchiolitis, asthma, and bronchiectasis there is a massive increase in the number and size of mucus secreting glands and cells with markedly increased production of mucus. This problem is made worse by damage to the airways leading to poor clearance of secretions. The build up of these mucus secretions in the airway further increases the amount of infection and inflammation, leads to increased difficulties in breathing, and can be associated with destruction of lung tissue. It is acknowledged that retention of airway secretions is an extremely important factor in the development of chronic lung disease and that medications to enhance clearance of these secretions could be of significant therapeutic benefit with potential to help tens of millions of Americans every year.

*The research laboratory of Dr. Bruce K. Rubin, one the inventors

In a series of experiments, we have determined that one of the most important factors influencing the ability to clear mucus secretions from the airways is the adhesiveness of these secretions and that this adhesiveness in turn was largely determined by the surface tension of the secretions in the airway. We then demonstrated that surfactants have the ability to reduce the adhesiveness of secretions and that this in turn, significantly enhances both cough and mucociliary clearance. To put this into perspective, imagine if you will, a child shooting objects from a pea shooter. In order to expel a small wad of sticky substance that attaches to the inside wall of the pea shooter it will take much more effort and airflow from the child then it would to shoot out a pea that has been lubricated by a bit of spit. In this analogy, the pea shooter is the airway, the childś effort represents how hard one must cough to clear secretions, and the substances obviously represent sticky or lubricated airway secretions.

Research has shown that surfactant is not only produced in the alveoli but that surfactant phospholipids are also secreted from the mucus glands and larger airways. We have demonstrated that airway surfactant is essential for mucus clearance and we further demonstrated that in many of the pulmonary diseases associated with hypersecretion there was inactivation of surfactant by inflammatory mediators. Because of this we hypothesized that the administration of pulmonary surfactant to patients with cystic fibrosis or chronic bronchitis would enhance mucus clearance and improve pulmonary function.

OBJECTS AND SUMMARY OF THE PRESENT INVENTION

It is therefore an object of the present invention to use a surface-active agent to promote mucus clearance in patients with either mucus hypersecretion or with secretion retention.

It is a secondary object of the present invention to treat the disease known as meconium aspiration.

It is a third object of the present invention to use surfactant as lubricating agent for those having sleep apnea and accompaning snoring.

It is a fourth object of this invention to use a surfactant as a distributing agent for other medication throughout th airways.

We then conducted large, randomized, placebo-controlled, prospective, multi-center trials of aerosolized artificial surfactant (Exosurf(®), Glaxo Welcome. Research Triangle Park, N.C.) administered by aerosol to patients with chronic bronchitis and to patients with cystic fibrosis. In these studies, we evaluated pulmonary function measured by spirometry, patient well-being, and mucus properties as primary outcome variables and showed a dose-dependent improvement in pulmonary function and in the clearability of airway secretions in patients administered a surfactant aerosol but not a placebo. This is the first time that surface-active agents have been shown to be effective in promoting mucus clearance in patients with hypersecretion.

The safety of inhaled pulmonary surfactants has been well established by administration of this medication to tens of thousands of newborn infants around the world and to hundreds of adults with severe lung disease. Our studies also demonstrated an excellent safety profile for aerosol surfactant administration.

DETAILED DESCRIPTION OF THE PREFERRED EMBODIMENTS

There are two principal mechanisms for airway mucus clearance. In health, the overwhelmingly prominent mechanism is mucociliary clearance. The larger airways (bronchi and trachea) are lined with a specialized stratified columnar ciliated cell layer (epithelium). These cells each contain about 400 microscopic rapidly beating cilia that tend to serve to propel ciliated mucus up and out of the airways. By this action they are vital in rapidly "sweeping" the airway clear of foreign particles including bacteria and pollutants.

When there is damage to the epithelium there is a protective increase in the mucus-secreting cells and mucus production. There is also often damage to the sensitive ciliated cells. The result of this is poor mucociliary clearance and buildup and mucus containing bacteria, dead cells and cell products and neutrophils (pus cells). In persons with cystic fibrosis, chronic bronchitis, bronchiectasis and some forms of asthma, this leads to the expectoration of this material, called sputum or phlegm when it is coughed up. In this situation, the defense and clearance of the airway becomes much more dependent on cough or airflow-dependent clearance.

Following is a detailed report of our tests. This gives a detailed report of what we did, and provides a line by line summary of the dosages and results.

Chronic bronchitis affects approximately 13 million adults in the United States. This condition is characterized by bronchial mucus gland and goblet cell hyperplasia, and increased sputum production and decreased clearance. In normal subjects, a bronchial surfactant layer that reduces the sputum adherence to the epithelium has been demonstrated between the periciliary fluid and mucus. Bronchial surfactant has been shown to increase mucociliary clearance, stabilize airways, and reduce airway inflammation. Several investigators have demonstrated a decrease in the amount of bronchial surfactant in patients with chronic bronchitis and abnormal sputum phospholipid Composition. In established chronic bronchitis, sputum clearance becomes vitally important not only for maintaining pulmonary function, but also for reducing the burden of infection and inflammatory mediators.

We hypothesized that administration of exogenous aerosolized surfactant to patients with chronic bronchitis would increase sputum clearability, which in turn might result in improved pulmonary function. In order to test this hypothesis, we performed a prospective, randomized, double-blind study of three doses of surfactant or saline given by nebulization 3 times a day for 14 days to outpatients with stable chronic bronchitis. We studied the effects of aerosolized surfactant on sputum surface properties and transportability; pulmonary function (spirometry and lung volumes); and respiratory symptoms.

METHODS

Patients

This study was conducted between October 1994 and February 1995 in 87 patients with chronic bronchitis who were enrolled from fours centers within the United States. The protocol was approved by the Institutional Review Board of each participating center, and each patient provided written informed consent. Inclusion criteria included a diagnosis of chronic bronchitis, a smoking history of greater than 10 pack years, forced expiratory volume in ore second ($FEV_1$) 40 to 70% predicted of normal values, and a $FEV_1/FVC<70\%$ (FVC—forced vital capacity). Patients with a diagnosis of asthma or atopy; a concomitant life threatening disease; active pulmonary disease other than chronic bronchitis (e.g. bronchiectasis, emphysema, pneumonia, tuberculosis, lung cancer, cystic fibrosis); or an acute respiratory tract infection within the previous month were excluded. Patients who were using antibiotics, corticosteroids (more than 5 mg/day of prednisone or equivalent), codeine, iodinated glycerol, N-acetylcysteine, or other over-the-counter antitussives or mucoactive agents were also excluded.

The surfactant preparation used in this study was Exosurf® (Glaxo Wellcome, Inc., Research Triangle Park, N.C.), a synthetic surfactant containing a lipid component DPPC, and surface spreading components, tyloxapol and hexadecanol. Patients were randomized to receive one of three different doses of surfactant, either 202.5 mg DPPC/day, 607.5 mg DPPC/day, or 1215 mg DPPC/day, or 0.9% NaCl (saline). A random block design was used to ensure balance of study groups within each center. The study was conducted in three phases: screening, treatment, and post-treatment.

Screening Phase

Patients were enrolled after the inclusion criteria were met and then were followed for one week during which they continued their usual medications. At the end of this baseline period (day 0), patients returned to the pulmonary function laboratory. Patients were instructed not to use long-acting bronchodilators for at least 24 hours or short-acting bronchodilators for at least 12 hours, and not to ingest caffeine or chocolate for eight hours before this clinic visit. To ensure adequate compliance with these instructions, serum theophylline levels were monitored and required to be below 6 μg/ml on study days. Patients who met all requirements had spirometry (pre- and post-bronchodilator) and lung volumes performed. For safety, the first dose of study drug was given in the clinic, and 60 minutes later spirometry was repeated to ensure that pulmonary function ($FEV_1$ or FVC) did not decrease.

Treatment Phase

Study drug was prepared by diluting the Exosurf® formulation by adding sterile saline to a volume of 5 ml. Study drug was administered as an aerosol using a jet nebulizer (PARI LC Jet nebulizer, PARI Respiratory Equipment, Inc., Richmond, Va.) used for 15 minutes, 3 times a day for 14 consecutive days. Patients kept daily records of study drug use and changes in symptoms. Patients returned to clinic on day 14 after following the same procedures described above.

Posttreatment Phase

Patients were followed for an additional week after the treatment period and returned on day 21 for final testing following the same procedures described above, Patients completed a Respiratory Symptoms Questionnaire at all clinic visits.

Sputum Analysis

Expectorated sputum was collected during an eight hour period in a sterile cup on the day before coming to clinic. Patients were instructed to swallow all saliva before expectoration, and collected sputum was visually separated from saliva before being placed in an airtight container and stored at −70° C. until analyzed.

Sputum Surface Properties

Sputum adhesion tension γ by De Noüy ring method: A platinum-iridium ring, a metal that is completely wettable, was pulled from a sputum sample at a velocity of 10 ml/second until separation was achieved. The force of separation was measured by a semi-automated tensiometer (Fischer Tensiomat Model #21, Fischer Scientific, Pittsburgh, Pa.) connected to the ring. The results are reported in dyne/cm.

Sputum cohesiveness (spinnability): Cohesiveness is the thread forming ability of mucus under the influence of large amplitude deformation. The measurement was performed in a 25 μl sputum sample that was pulled apart at a velocity of 10 ml/second. An electric signal conducted through the sputum sample was interrupted at the point where the stretched sputum thread was broken. The distance represented the sputum cohesiveness (cm).

Transportability of Sputum

In vitro ciliary Transportability: An excised mucus-depleted palate from a mature leopard frog (*Rana pipiens*) was dissected and prepared as previously described. The palate was placed in a humidified Plexiglas container and focused under a microscope so that a 12.7 μm scale was positioned between the optic bulges to the opening of the esophagus. The movement of a 5 μl sputum specimen was timed as the trailing edge moved across a 7.62 μm segment. Three measurements of mucociliary transportability were taken, and the average transport rate was normalized to the transport rate of endoganous frog mucus.

In vitro cough transportability: A model Plexiglas trachea, rectangular in cross section (1.2×2 cm), was connected to an 8 L tank that contained air pressurized to 8 PSI given a flow rate of about 11 L/second. This flow rate was equivalent to the peak transient flow of a natural cough. The characteristics of this apparatus had been previously validated. A sputum sample, 40 μl in volume and 0.5 μm in depth, was placed across a cough machine, The bulk transport of the sample was measured after each cough maneuver. Three successive maneuvers were obtained and the results averaged.

Pulmonary Function Measurements

Spirometry was performed on the morning of each visit according to American Thoracic Society guidelines. All measurements were made with the subject in the sitting position and using a nose clip. Three reproducible flow-volume curves with less than 10% variability in $FEV_1$ were measured before and 15 minutes after albuterol, 180 μg (2 puffs) via a metered dose inhaler.

Respiratory Symptoms

A Respiratory Symptoms Questionnaire previously validated by Petty, et al assessed cough frequency and severity, chest discomfort, dyspnea, ease of bringing up sputum, and need for additional aerosol bronchodilator. Data were analyzed by individual domain, as an aggregated score, and as a global evaluation by the investigator.

Statistical Methods

Demographic characteristics were collected from all subjects enrolled in the study. These were analyzed for comparability between the treatment groups using a Chi-Square test, unpaired t-test, and the Wilcoxon Rank Sum Test. Efficacy analysis was performed on data from all subjects who completed the treatment period. Percentages of predicted spirometry values (pre- and post-bronchodilator $FEV_1$, FVC) and lung volumes (total lung capacity and residual volume) were calculated using Morris Standards. Percentage change from baseline [(posttreatment—pre-treatment)/pre-treatment] for each measurement at days 14 and 21 was also calculated. Actual values of data were compared within treatment groups with paired t-test and between groups using analysis of variance (Student-Neuman-Keul). The number of adverse events was compared between the surfactant and placebo groups using the Wilcoxon Rank Sum Test. Actual values of sputum properties were analyzed within treatment groups with paired t-test. Pearson correlation logistic regression analysis was performed to assess sputum surface properties and transportability. The log of sputum tenacity was the dependent variable, and cough clearability was the independent variable in this model. In order to detect a 10% difference in pre- and posttreatment drug measurements, we calculated that 20 patients should be enrolled in each group. This sample size would provide the study with 95% power to detect a 10% relative improvement in sputum clearance and pulmonary function with surfactant treatment. Data are presented as means (SEM).

RESULTS

Patients

The study population consisted of 87 patients (71 male and 16 female), 21 in the saline group and 66 in the surfactant groups (202.5 mg DPPC/day=21, 607.5 mg DPPC/day=22, and 1215 mg DPPC/day =23). Demographic characteristics and baseline spirometry were similar between study groups (Table 1). Smoking history was also similar between groups; 39% of patients in the control group were current smokers and 61% were former smokers, and 43% of patients in the surfactant groups were current smokers and 57% were former smokers ($p=0.882$).

Of the 87 study patients, 79 completed the two week treatment period. In the placebo group, one patient did not complete the study due to acute exacerbation of chronic bronchitis. In the 202.5 mg DPPC/day surfactant group, two patients did not complete the treatment period due to acute exacerbation of chronic bronchitis, and one patient, due to subjective fever and malaise. In the 607.5 mg DPPC/day surfactant group, one patient did not complete the study period due to acute exacerbation of chronic bronchitis. In the 1215 mg DPPC/day surfactant group, one patient did not complete the study period due to confusion and neck side pain, one due to acute exacerbation of chronic bronchitis, and one due to anxiety. In no case did the investigator attribute the acute exacerbation to study medication.

Sputum Analysis

Sputum samples were available from 76 patients.

here was a dose-dependent increase in mucociliary transportability of expectorated secretions measured in vitro. The sputum obtained at the start of the study was compared to secretions obtained two weeks after treatment (saline=−4%, 202.5 mg DPPC/day surfactant=+7%, 607.5 mg DPPC/day surfactant=+29%, and 1215 mg DPPC/day surfactant=+22%) ($p=0.04$). There was a trend toward decreased sputum cohesiveness in the patients receiving 607.5 mg DPPC/day of surfactant ($p\leqq 0.11$). Logistic regression analysis of sputum transportability was correlated with the changes in sputum tenacity (FIG. 2). These data showed that decreased sputum tenacity resulted in increased cough clearance in the surfactant treated subjects ($p<0.0001$, $r=-0.60$).

Pulmonary Function Measurements

The 607.5 mg DPPC/day surfactant group had significant increases pre- and post-bronchodilator in $FEV_1$ and FVC by days 14 and 21 as compared to day 0. The absolute change in FVC was greater than 200 ml in the 607.5 mg DPPC/day surfactant group by day 14, and 280 ml increase in the 1215 mg DPPC/day group by day 21. No significant changes in spirometry were noted in the saline and 202.5 mg DPPC/day surfactant groups.

In order to identify if specific patients responded differently to exogenous surfactant, two post-hoc analyses were done. The first analysis was based on patients' pre-bronchodilator $FEV_1$ at baseline as an indication of severity of disease. Patients were divided into two groups: baseline $FEV_1<55\%$ of predicted (n=63) or $FEV_1>55\%$ of predicted (n=17). A 10% increase in pre-bronchodilator $FEV_1$ on day 14 and a 13.43% increase on day 21 as compared to day 0 was seen in the 607.5 mg DPPC/day surfactant group with a baseline $FEV_1<55\%$ of predicted ($p\leqq 0.05$). In the patient group treated with 1215 mg DPPC/day surfactant, pre-bronchodilator $FEV_1$ increased 18% on day 21 as compared with day 0 ($p<0.05$). No statistical comparisons were done in the baseline $FEV_1>55\%$ predicted group because of the small number of patients.

The second post-hoc analysis was based on selection of patients with bronchial hyperresponsiveness using the American Thoracic definition. Patients were divided at baseline into two groups: 1) those with <15% (n=42) increase in post-bronchodilator $FEV_1$; and 2) those with >15% (n=35) increase in post-bronchodilator $FEV_1$. In patients without bronchial hyperresponsiveness (<15% bronchodilator response), a significant improvement in pre-bronchodilator $FEV_1$ was observed at days 14 and 21 in the 607.5 mg DPPC/day surfactant group.

The absolute values for residual volume (RV) and total lung capacity (TLC) were similar between treatment groups at any study time. However, the RV/TLC had decreased 6% by day 21 in both the 607.5 mg DPPC/day and 1215 mg DPPC/day surfactant groups as compared with the saline group ($p\leqq 0.05$).

Respiratory Symptoms

Respiratory Symptoms Questionnaires were completed on days 0, 14 and 21. Cough frequency, ability to bring up sputum, aggregated score, and global evaluation were all improved significantly on days 14 and 21 compared to day 0 in both surfactant and saline study groups ($p\leqq 0.05$), but there was no significant difference in the degree of improvement between groups.

DISCUSSION

In this study we showed that 14 days of aerosolized surfactant (607.5 mg DPPC/day) increased in vitro sputum transportability, improved pre- and post-bronchodilator $FEV_1$ and FVC by more than 10% , and decreased trapped thoracic gas (RV/TLC ratio) by more than 6% in patients with stable chronic bronchitis. This effect persisted at least a week after treatment was completed. A post-hoc analysis showed that the effect of aerosolized surfactant was more significant in patients who had lower initial $FEV_1$ or <15% improvement in post-bronchodilator $FEV_1$. These findings support the hypothesis that this improvement in pulmonary functions was due, in part, to improved sputum clearance.

Medical care for patients with chronic obstructive lung disease has recently been outlined, but did not address any therapy for the increased sputum production seen in these patients. Treatments that have been proposed for mobilizing airway secretions include hydration, mucolytic drugs such as N-acetylcysteine, or expectorants such as ionated glycerol. In carefully controlled trials, none of these agents has demonstrated clear benefit in improving pulmonary function or sputum clearance. The only mucoactive agent approved for use in the United States is rhDNase (Pulmozyme®, Genentech, South San Francisco, Calif.), and this is only approved for the treatment of cystic fibrosis lung disease. Pulmozyme® has been shown to reduce the viscosity and adhesiveness of infected sputum in vitro and produce a modest improvement in $FEV_1$. In patients with chronic bronchitis, a trial of aerosolized Pulmozyme® administered during acute exacerbations did not result in improved pulmonary function, but appeared to reduce mortality. However a larger study refuted these earlier results. In this study, we showed that giving aerosolized surfactant improved sputum mucociliary transportability, increased airflow and decreased dynamic hyperinflation (RV/TLC ratio). This effect was more pronounced in patients with worse lung function, and independent of the subject's baseline bronchodilator response. Furthermore, the changes in spirometry were greater than the ones reported with the use of Pulmozyme® in cystic fibrosis.

An important determinant of the effects of exogenous surfactant is its ability to spread into the airway. In an in vitro model, Espinosa, et al showed that exogenous surfactant spreads into the distal airway, and this effect is enhanced by the amount of material delivered up to the point of saturation. From the clinical results obtained in this study, we speculate that 607.5 mg DPPC/day of surfactant achieved coverage of the conductive airways to saturation. We believe that this effect could explain why the 1215 mg DPPC/day surfactant group had similar changes in lung function. However, in vitro analysis of sputum clearance showed a dose-related effect.

Isotonic saline (0.9% NaCi) was used in the control group and as the excipient for surfactant because it is well tolerated. However, we found that saline was not inert. The saline-treated patients showed a less than 4% improvement in pulmonary function and in respiratory symptoms. Because statistical analysis compared the saline group to each of the surfactant-treated groups, the benefit of surfactant treatment may, therefore, have been underestimated.

The different physical characteristics of saline and surfactant could have led to unintentional unblinding of the study. However, we took careful precautions to minimize this problem, including the use of opaque study drug containers and nebulization lines, as well as limiting the communication between patients. Furthermore, the staff performing the efficacy evaluations and the evaluating physicians were separated from those who provided study drug. Because of these precautions, we believe that we have minimized the possibilities of unblinding.

The improvement in pulmonary function and decrease in trapped gas was not only seen when the patients were using the study drug, but persisted up to a week after therapy was discontinued. However, the change in sputum characteristics was present only during active administration of surfactant. This is consistent with the primary effect of surfactant therapy being that of improving the clearability of secretions, resulting in improved airflow and a reduction in trapped thoracic gas.

CONCLUSIONS

This study shows a very small but statistically significant improvement in sputum characteristics and post bronchodilator spirometry associated with the use of aerosolized artificial surfactant. Furthermore, this study is the first one to demonstrate that changes in sputum clearance may result in an improvement in lung spirometry.

HYPOTHESIS

We have hypothesized beyond the foregoing that mucus secretions can be further eliminated by the addition of a hyperosmolar agent.

The most important determinations of cough clearability are air flow (gas-liquid pumping in more peripheral airways), or how hard the patient can cough, in larger airways, and sputum adhesion or the extent to which it sticks to the epithelium. The greater the airflow velocity the more effective the cough. As well the stickier the mucus or sputum the less effective coughing will be. The viscosicity of sputum is not markedly abnormal in cystic fibrosis or bronchitis but the sputum is very sticky and we have shown that cough clearance and pulmonary function can be improved by using surfactant aerosol therapy. Surfactant also has a beneficial effect on mucociliary clearance, enhancing energy transfer from cilia to the mucus gel, however, this effect is less profound. Surfactant also has a property of rapid and complete distribution or spreading through the entire airway by virtue of its ability to lower surface tension. Surfactants have been used to enhance the distribution of therapeutic agents, such as Pentamidine aerosol used to treat pneumocystis cariniipneumonia.

From the foregoing it will be seen that "optimal" therapy for clearing the airway abnormal secretions would be able to maximize both mucociliary and cough clearance and this medication should be able to reach even severely obstructed airways. The therapy should be as long lasting as possible, easily delivered to the airways "by nebulization or by metered dose or by dry powder inhaler", of relatively low cost, safe to the patient (e.g. free of significant side effects, and if possible able to reduce infection or inflammation directly). Appropriate hydration of airway secretion is best accomplished by adequately hydrating the patient, but inhaled aqueous mist may retard insensible water loss from the airway. Over-hydration can lead to mucosal edema and reduce mucus clearance. Patients with asthma can develop bronchospasm following saline or water nebulization, or exposure to cold inhaled mist. Moderately increased systemic hydration in patients with chronic bronchitis exerts little effect on sputum—or ease of expectoration.

We therefore propose to patent the novel concept of using a surface-active agent to promote mucus clearance in patients with either mucus hypersecretion or with secretion retention. This proposal would include all surfactant preparations that are presently available including those mentioned above, all surface active agents that reduce the surface tension and adhesiveness of airway secretions, including but not limited to those containing dipalmitoyl phosphotidylcholine (DPPC). and all methods of administering this surfactant to the airway including but not limited to metered dose inhalation, dry powder inhalation, jet nebulization, and ultrasonic nebulization.

A second application of surfactants as lubricating agents is as a treatment for the disease known as meconium aspiration syndrome. This disease occurs in newborn babies who have inhaled fecal material while still in the uterus. Generally this occurs as a result of passage of the first stool, called meconium at a time of intrauterine stress. Meconium has been shown to inactivate surfactant and lead to extreme respiratory distress usually requiring assisted ventilation and frequently death in babies who inhale it. We have demonstrated that surfactant can rapidly reduce the stickiness of meconium making it easier to remove from the infants lungs and reducing the risk of severe injury and even death. This second application of surfactant as a lubricating agent is very similar to the proposal to use surfactant to reduce the stickiness of mucus.

A third use of surfactant as a lubricating agent is to reduce airway obstruction and snoring in patients with obstructive sleep apnea. Obstructive sleep apnea occurs when the tongue and the pharynx (the back of the nose and throat) come together in sleep preventing the passage of air. This is often indicated by loud snoring with the respiratory pauses ill sleep, sleep interruption, daytime sleepiness, and lack of energy. Sleep apnea is thought to be responsible for many missed days of work, loss in productivity, and even motor vehicle accidents with sufferers falling asleep at the wheel because of poor sleep quality. A number of surgical and non-surgical techniques have been advocated to minimize upper airway obstruction. There is evidence that reducing the stickiness of the tongue to the pharynx by using a lubricating agent such as surfactant will make it less likely that persons snoring will obstruct their airway and develop sleep apnea.

We therefore propose in patent the use of any form of surfactant as a lubricating agent to prevent airway obstruction and to facilitate the removal of the material from the airway including mucus, retained secretions, and foreign material such as meconium.

An additional function of surfactant is as a spreading agent that will improve the distribution of other medications throughout the airway. As surfactant spreads throughout the airway, it has the ability to carry other medications with it to the lower respiratory tract. Therefore we also propose the use of surfactant as a surface tension lowering agent to enhance the distribution and spreading of other medications to the lower respiratory tract, specifically surfactant administered with an antibiotic aerosol for the treatment of lower respiratory tract infections in patients with cystic fibrosis, chronic bronchitis, or bronciectasis and for treating pneumocystis carinii pneumonia in AIDS or other conditions usually but not necessary or limited to immunodeficiency. We also proposed the use of surfactant as a spreading agent to enhance the distribution of mucoactive agents such as hyperosmolar solutions or rhDNase to the lower respiratory tract of patients with chronic secretion retention. And this proposal includes the use of surfactant to enhance the distribution of inhaled anti-inflammatory agents and bronchodilators to the lower respiratory tract of patients with asthma or other conditions characterized by reversible airflow obstruction due to conditions of the upper respiratory tract such as, but not limited to rhinitis, nasal polyposis, sinusitis, laryngitis, croup, bronchitis, emphysema, bronchiolitis or alveolitis from any cause.

The use of hypertonic saline as a possible expectorant has recently attracted attention. The inhalation of hypertonic saline (generally 4.5 ml. of 3–6% saline by jet or ultrasonic nebulization) has been used for sputum induction to evaluate for the presence of neoplastic cells, tuberculosis, or phenmocystis. This technique has also been used experimentally to obtain airway cells in patients with asthma. Short term studies suggest that the inhalation of 6% saline can increase expectoration and improve pulmonary function and quality of life in patients with cystic fibrosis. Because hypertonic saline is inexpensive and readily available, this could be an attractive therapy to enhance secretion clearance.

It will now be apparent that we have disclosed a medicine comprising a mix of surfactant with means to convert the medicine to an aerosol, and some drugs known to promote spreading. Hypersmolar drugs have been suggested as an addition to help minimize mucus. These will be helpful to veterinary doctors as well. They will be of help in clearing the airways of most patients suffering from impairment of the airways. The addition of some other drugs including those for patients with cystic fibrosis, asthma, or chronic fibrosis is also a subject of the present invention. In the claims it will be understood that aerosolized is to include either wet or dry. The hyper-hyperosmolor drugs can be of any kind.

The invention is claimed as follows:

1. A method for the treatment of the respiratory tract when one or more of the following condition is present, adhesiveness of the inflammatory cells to tissues, excessive adhesiveness of mucus to tissues or mucus collections in the respiratory tract, wherein the method consists of administering a medicine aerosol that consists of a phospholipid surfactant in said aerosol to the patient resulting in the phospholipid surfactant being the sole medication deposited in the lungs and air passages of the patient.

2. A method for the treatment of the respiratory tract when one or more of the following condition is present, adhesiveness of inflammatory cells to tissues, excessive adhesiveness of mucus to tissues or mucus collections in the respiratory tract when accompanied by one or more of cystic fibrosis, chronic fibrosis, asthma, or bronchitis, wherein the method consists of administering a medicine aerosol that consists of a phospholipid sufactant plus one or more medicines effective against cystic fibrosis, chronic fibrosis, asthma, or bronchitis distributed in said aerosol to the patient resulting in the phospholipid surfactant accompanied by the one or more medicines being the only medicines being deposited in the lungs and air passages of the patient.

3. A method for the treatment of the respiratory tract when one or more of the following condition is present, adhesiveness of the inflammatory cells to tissues, excessive adhesiveness of mucus to tissues or mucus collections in the respiratory tract, wherein the method consists of administering a medicine aerosol that consists of a phospholipid surfactant and a hypersmolar compound in said aerosol resulting in the phospholipid surfactant and the hyperosmolor compound being the sole medication deposited in the lungs and air passages of the patient.

* * * * *

US005925334C1

(12) EX PARTE REEXAMINATION CERTIFICATE (4980th)

United States Patent

Rubin et al.

(10) Number: US 5,925,334 C1

(45) Certificate Issued: Aug. 24, 2004

(54) USE OF SURFACE ACTIVE AGENTS TO PROMOTE MUCUS CLEARANCE

(75) Inventors: Bruce K. Rubin, 2140 Royall Dr., Winston-Salem, NC (US) 27106; Michael T Newhouse, Hamilton (CA)

(73) Assignee: Bruce K. Rubin, Winston-Salem, NC (US)

Reexamination Request:
No. 90/006,315, Jun. 27, 2002

Reexamination Certificate for:

| | |
|---|---|
| Patent No.: | **5,925,334** |
| Issued: | **Jul. 20, 1999** |
| Appl. No.: | **08/918,112** |
| Filed: | **Aug. 27, 1997** |

(51) Int. Cl.[7] .................................................. A61K 9/12

(52) U.S. Cl. ........................... 424/45; 424/46; 514/851; 514/826; 514/75; 514/78

(58) Field of Search ....................... 424/45, 46; 514/75, 514/78

(56) References Cited

U.S. PATENT DOCUMENTS

| | | | |
|---|---|---|---|
| 5,262,405 A | 11/1993 | Girod-Vaquez et al. | |
| 5,299,566 A | 4/1994 | Davis et al. | |
| 5,306,483 A | 4/1994 | Mautone | |
| 5,698,537 A * | 12/1997 | Pruss | 514/78 |

OTHER PUBLICATIONS

Rubin, et al. "Mucus Rheology and Transport in Neonatal Respiratory Distress Syndrome and the Effect of Surfactant Therapy*" Chest, vol. 101, p. 1080–1085 (1992).

Rubin, "A Superficial View of Mucus and the Cystic Fibrosis Defect", Pediatric Pulmonology, vol. 13, pp. 4–5 (1992).

De Sanctis, et al., "Exogenous surfactant enhances mucciliary clearance in the anaestheized dog", Eur. Respir. J., vol. 7, pp. 1616–1621 (1994).

Albers, et al., "Ring distraction technique for measuring surface tension of sputum: relationship to sputum clearability" American Physiological Society, pp. 2690–2695 (1996).

Anzueto, et al., "Effects of Aerosolized Surfactant in Patients WIth Stable Chronic Bronchitis", J. Am. Med. Assoc., vol. 278, pp. 1426–1431 (1997).

* cited by examiner

*Primary Examiner*—Mina Haghighatian

(57) ABSTRACT

This disclosure is of a surfactant mixed with an aerosollizing agent, and deposited by such agent, as a treatment for airway obstruction. It has been extensively tested, and has proved successful. It has been hypothesized that the addition of a hypersmolor drug will help to minimize mucus in the airways.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 3 are determined to be patentable as amended.

New claims 4 and 5 are added and determined to be patentable.

1. A method for the treatment of the respiratory tract when one or more of the following condition is present, adhesiveness of the inflammatory cells to tissues, excessive adhesiveness of mucus to tissues or mucus collections in the respiratory tract, wherein the method consists of administering a medicine aerosol that consists of a phospholipid surfactant in said aerosol to the patient resulting in the phospholipid surfactant being the sole medication deposited in the lungs and air passages of the patient *wherein the amount of phospholipid surfactant administered to the patient ranges from 202.5 milligrams per day to 1215 milligrams per day*.

2. A method for the treatment of the respiratory tract when one or more of the following condition is present, adhesiveness of inflammatory cells to tissues, excessive adhesiveness of mucus to tissues or mucus collections in the respiratory tract when accompanied by one or more of cystic fibrosis, chronic [fibrosis] *bronchitis*, asthma, or bronchitis, wherein the method consists of administering a medicine aerosol that consists of a phospholipid [sufactant] *surfactant* plus one or more medicines effective against cystic fibrosis, chronic [fibrosis] *bronchitis*, asthma, or bronchitis distributed in said aerosol to the patient resulting in the phospholipid surfactant accompanied by the one or more medicines being the only medicines being deposited in the lungs and air passages of the patient *wherein the amount of phospholipid surfactant administered to the patient ranges from 202.5 milligrams per day to 1215 milligrams per day*.

3. A method for the treatment of the respiratory tract when one or more of the following condition is present, adhesiveness of the inflammatory cells to tissues, excessive adhesiveness of mucus to tissues or mucus collections in the respiratory tract, wherein the method consists of administering a medicine aerosol that consists of a phospholipid surfactant and a hypersmolar compound in said aerosol resulting in the phospholipid surfactant and the hyperosmolor compound being the sole medication deposited in the lungs and air passages of the patient, *wherein the amount of phospholipid surfactant administered to the patient ranges from 202.5 milligrams per day to 1215 milligrams per day*.

*4. A method for the treatment of the respiratory tract when one or more of the following condition is present, adhesiveness of the inflammatory cells to tissues, excessive adhesiveness of mucus to tissues or mucus collections in the respiratory tract, wherein the method consists of administering a medicine aerosol that consists of dipalmitoyl phosphotidylcholine in said aerosol to the patient resulting in the dipalmitoyl phosphotidylcholine being the sole medication deposited in the lungs and air passages of the patient, wherein the amount of dipalmitoyl phosphotidylcholine administered to the patient ranges from 202.5 milligrams per day to 1215 milligrams per day.*

*5. A method for the treatment of the respiratory tract when one or more of the following condition is present, adhesiveness of inflammatory cells to tissues, excessive adhesiveness of mucus to tisues or mucus collections in the respiratory tract when accompanied by one or more of cystic fibrosis, chronic bronchitis, asthma, or bronchitis, wherein the method consists of administering a medicine aerosol that consists of dipalmitoyl phosphotidylcholine plus one or more medicines effective against cystic fibrosis, chronic bronchitis, asthma, or bronchitis distributed in said aerosol to the patient resulting in the dipalmitoyl phosphotidylcholine accompanied by the one or more medicines being the only medicines being deposited in the lungs and air passages of the patient, wherein the amount of dipalmitoyl phosphotidylcholine administered to the patient ranges from 202.5 milligrams per day to 1215 milligrams per day.*

* * * * *